United States Patent [19]

Miller

[11] Patent Number: 4,593,788
[45] Date of Patent: Jun. 10, 1986

[54] RESCUE APPARATUS

[76] Inventor: Larry Miller, P.O. Box 784, La Canada, Calif. 91011

[21] Appl. No.: 581,575

[22] Filed: Feb. 21, 1984

[51] Int. Cl.⁴ .............................................. A61F 5/04
[52] U.S. Cl. ................................... 182/3; 128/87 R; 128/134
[58] Field of Search ................. 182/3; 128/87 R, 134, 128/133, 76 R

[56] References Cited

U.S. PATENT DOCUMENTS

| | | | |
|---|---|---|---|
| 1,301,276 | 4/1919 | Kroetz | 128/76 R |
| 2,735,424 | 2/1956 | Benjamin | 128/87 B |
| 3,697,065 | 10/1972 | Glassburner | 128/76 R |
| 4,143,654 | 3/1979 | Sherman | 128/134 |
| 4,182,322 | 1/1980 | Miller | 128/76 R |
| 4,211,218 | 7/1980 | Kendrick | 128/87 R |
| 4,422,454 | 12/1983 | English | 128/134 |

OTHER PUBLICATIONS

Med Spec, Charlotte, N.C., XP-One Instructions.
Med Spec, Charlotte, N.C., Extrication Plus by Med Spec, The Flexible System.
Two Photographs (Front and Backsides) of Another Prior Art Device (Vest).
Medical Specialties, Inc., Application of Device, Jun. 9, 1980, File #1532-44.
Medical Specialties, Inc., Introduction, Jun. 9, 1980, File #1532-44.

Primary Examiner—Reinaldo P. Machado
Attorney, Agent, or Firm—Knobbe, Martens, Olson & Bear

[57] ABSTRACT

A rescue vest is provided with a pocket extending along the spine area in the back of the vest. A thin, flat, elongated stiffener is removably positioned in the pocket and a head support and protector is removably positioned on the upper end of the stiffener. The vest can be positioned on and strapped to a person's torso, with the stiffener being used to immobilize the person's spine and neck. The vest may be positioned on the person without the stiffener and the stiffener then inserted into the vest. Groin straps attached to the lower portion of the vest enable a person to be lifted by means of the vest. Thus, without the stiffener, the vest may be used for lifting or lowering a rescuer.

11 Claims, 6 Drawing Figures

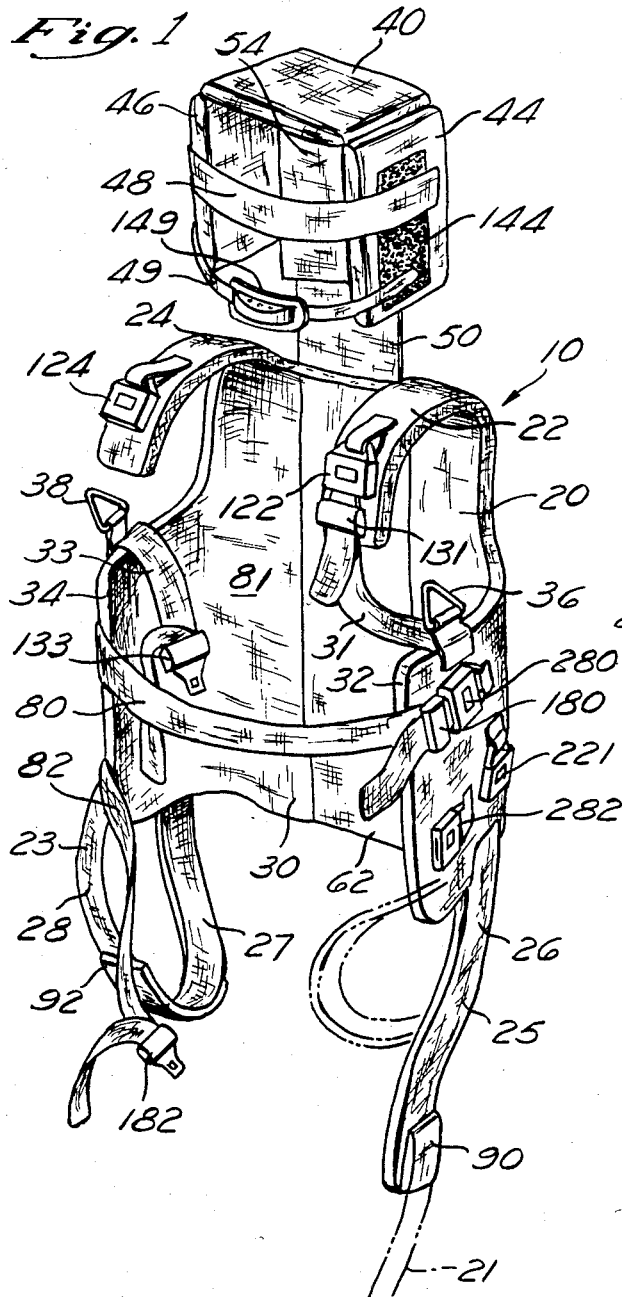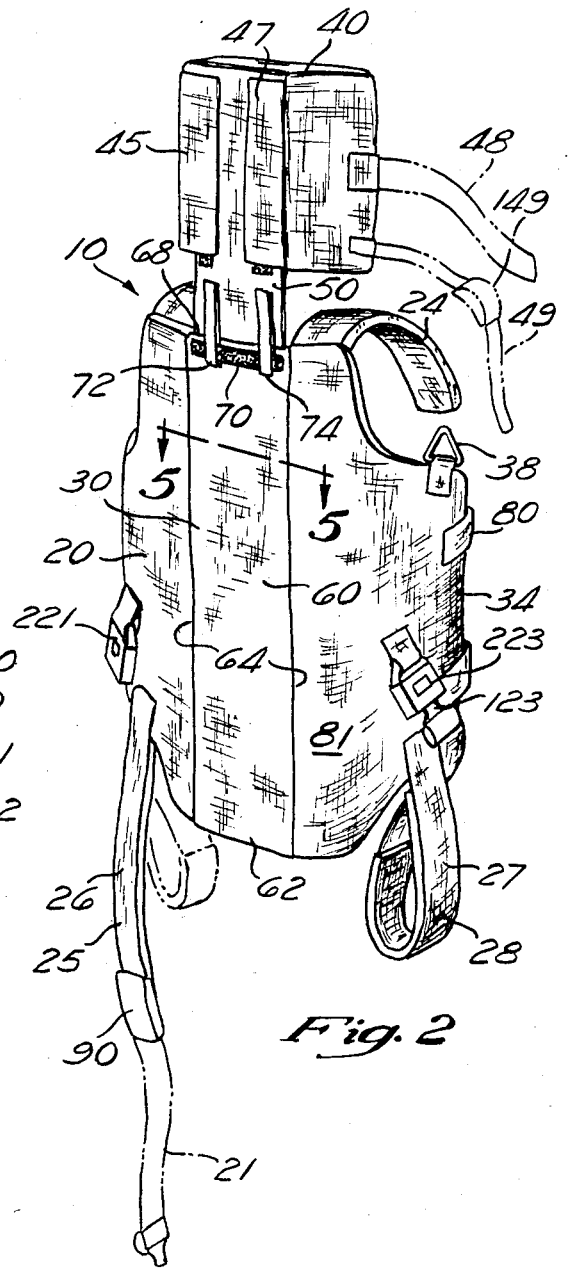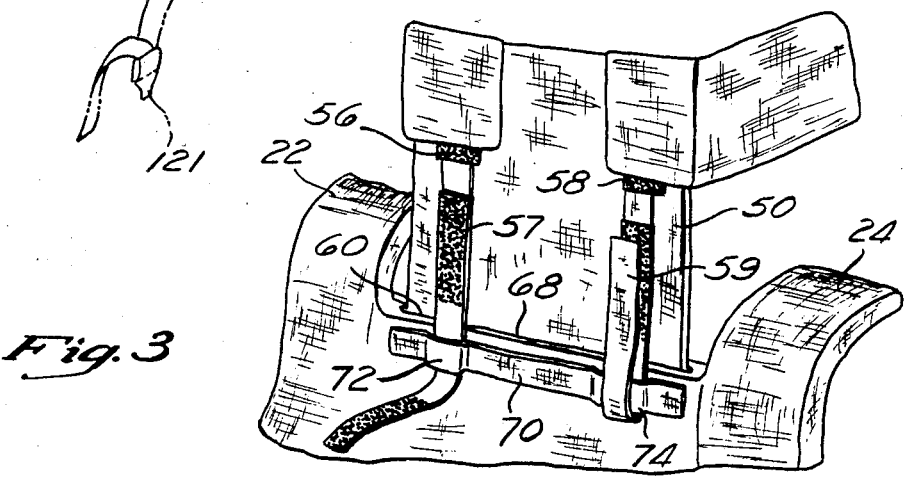

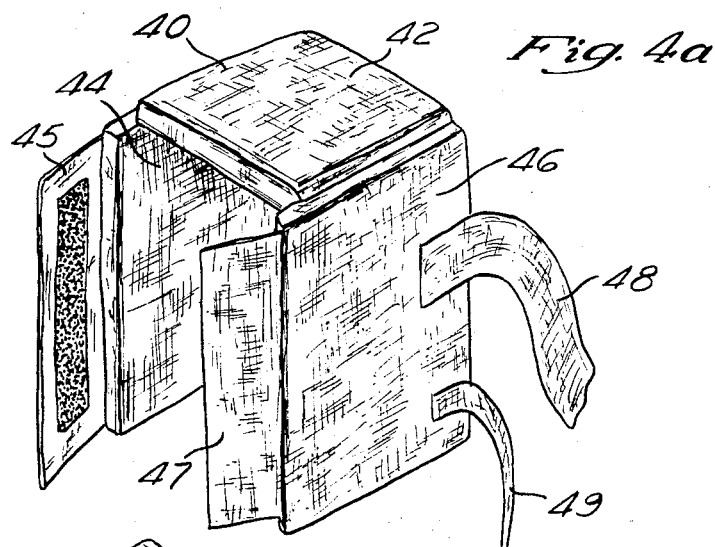
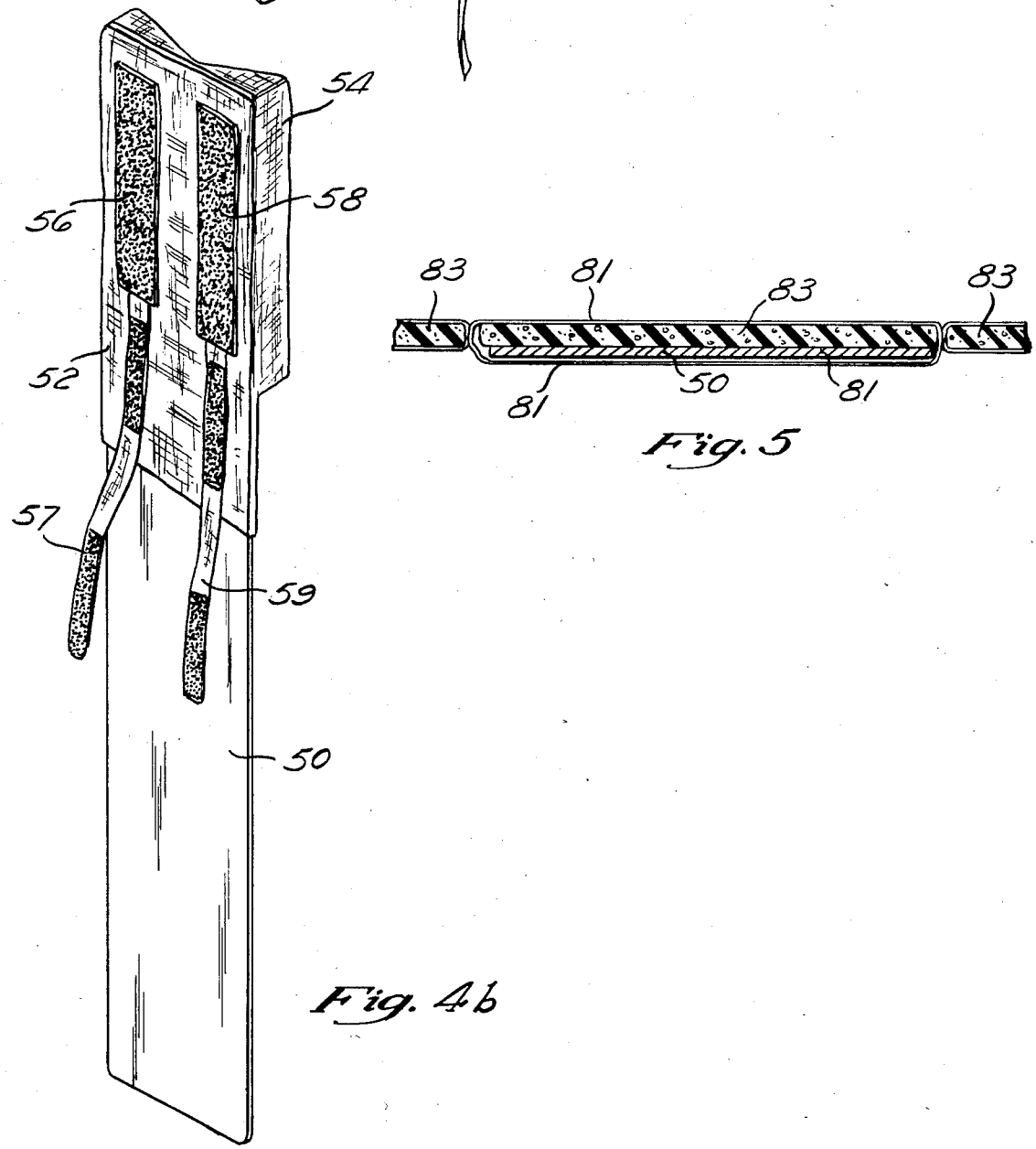

RESCUE APPARATUS

BACKGROUND OF THE INVENTION

This invention relates to rescue apparatus and more particularly to a novel vest-like harness to be utilized by a person to be rescued or by a rescuer in emergency accident situations.

One application which for this invention is particularly useful is for the rescue of accident victims that have spinal injuries. Spinal injuries can occur in many situations such as accidents in automobiles, athletics, and swimming pools. After a spinal injury, it is absolutely vital to keep the victim's spine and head immobilized as movement could cause further injury and, quite possibly, paralysis below the point in the spine where the injury occurred.

Previously, accident victims with spinal injuries or even suspected spinal injuries have been immobilized with spinal boards. Spinal boards consist of a board with tie downs. Rolled-up cloth or some other similar means was used to immobilize the victim's head. Many shortcomings exist with spinal boards. The boards are generally the length of a person's body and, consequently, are cumbersome and awkward in certain rescue operations. For example, a spinal board cannot be placed on a person's back when trying to rescue him from an automobile wreck. The person must be moved before a spinal board can be utilized.

Because of the shortcomings associated with spinal boards, a more sophisticated spinal restraint device was developed. The spinal restraint device essentially consists of a body wrap enclosing a series of rigid slats. The length of the slats is approximately equal to the dimension from slightly below the waist to approximately the top of the head of the victim. Several wings are attached to the main portion of the body wrap which wrap around the person's chest and mid-section as well as the sides of the victim's head. These wings also contain slats. Shortcomings also exist with this type of device. The spinal restraint device is not flexible and therefore many times may produce discomfort when being placed upon a victim. This device also causes further discomfort as the slats are wrapped around the person's head and mid-section. The spinal restraint is also absent any shoulder portions to restrict possible vertical downward movement of the device. In addition, the device cannot be used by itself to lift a person from an accident site.

SUMMARY OF THE INVENTION

The rescue apparatus disclosed herein overcomes many of the shortcomings of the prior art. The device has a padded head immobilizer as well as a padded body vest to maximize the comfort of a victim or other wearer of the rescue apparatus. Furthermore, the invention disclosed has a thin, wide removable spine stiffener. The wide stiffener allows the area around the spinal cord to be fully immobilized, yet does not make the rescue apparatus cumbersome. Furthermore, the removable feature is advantageous in that the rescue apparatus can be placed on a victim and then the stiffener inserted after placing the apparatus on the victim. Still a further advantage of the rescue apparatus disclosed is that it has shoulder straps and groin straps which virtually restrict all vertical movement of the rescue apparatus when properly worn.

Additionally, the rescue apparatus disclosed features lifting loops for connecting the rescue apparatus to a rescue line. This feature provides for a much more versatile rescue device than the prior art. The rescue device disclosed can be used to lift a rescuer to an accident site, then placed on the victim and used to lift the victim from the accident site. A helicopter or some other arrangement can then be used to move the victim to safety or a nearby site for transport.

The rescue apparatus disclosed also features a removable stiffener to immobilize the victim's spine. The removable stiffener adds to the versatility of the rescue apparatus. In certain situations the rescuer might not want to use the stiffener or the rescue apparatus can be eased onto the victim and then the stiffener can be inserted in the pocket after the body vest of the rescue device is in place. The stiffener can also be adapted for use in specialized situations. For example, the stiffener and head immobilizer could be adapted to hold a football player's or race car driver's head stationary by attaching directly to the victim's helmet. Several types of specialized stiffeners could be purchased for particular specialized applications. The same vest could then be used in various specialized applications with the stiffeners being interchangeable.

These and other advantages are discussed in the remaining portion of the specification which follows.

BRIEF DESCRIPTION OF THE DRAWINGS

FIG. 1 is a front perspective view of the rescue apparatus.

FIG. 2 is a rear perspective view of the rescue apparatus.

FIG. 3 is a perspective view of the stiffener and restraining means connected to the back portion of the rescue apparatus.

FIG. 4a is a perspective view of the head immobilizer shown detached from the stiffener.

FIG. 4b shows a rear perspective view of the stiffener with the rear head pad attached.

FIG. 5 is a cross-sectional view of the back portion of the rescue apparatus taken along line 5—5 in FIG. 2.

DESCRIPTION OF THE PREFERRED EMBODIMENT

The rescue apparatus 10 comprises a vest 20, a head immobilizer 40, and a stiffener 50. The vest comprises a back portion 30, with a pocket 60, two front body portions 32,34, and two shoulder portions 22,24. The vest is comprised of a flexible fabric 81, such as nylon, sewn to form a double layer or envelope of flexible material enclosing inner cushion material 83, as seen in FIG. 5.

The vest back portion 30 extends from slightly below the waist of the wearer to slightly above the shoulder blade of the wearer. Sewn on the outside of the back portion 30 is an elongated pocket 60, also made of a flexible fabric 81, such as nylon. The pocket 60 extends throughout the length of the back portion 30 along the spine of the wearer. The width of the pocket 60 will be at least 3 inches and will generally be slightly wider than the width of the human hand. The pocket 60 is formed with a closed lower end 62 proximate the bottom of the vest back portion 30, and closed sides 64. The upper end 68 of the pocket is open, terminating proximate the lower neck of the wearer. A restrainer strap 70 extends horizontally across the top of the vest back portion 30 near the pocket open end 68. The length of the horizontally extending restrainer strap 70 is approximately equal to the distance between the shoulder blades of the wearer. The strap is sewn on the outside surface of the pocket 60 and the back portion 30, in a manner to form two loops 72,74 with the back.

Twoo elongated shoulder portions 22,24 extend from the top of the vest back portion 30 over the wearer's shoulders when worn. Affixed proximate the end of each respective shoulder portion 22,24 is a female portion 122,124 of a buckle assembly.

The vest front portions 32,34 extend laterally from each side of the back portion 30 and extend approximately from slightly below the armpit to slightly above the waist of the wearer. Affixed to the upper edge of each front portion 32,34, proximate to the vertical side of each front portion 32,34 of the body vest 20 is a shoulder strap 31,33 made from a strong fabric such as nylon webbing. Within the length of each shoulder strap is an adjustable male portion 131,133 of the buckle assembly. The shoulder strap 31,33 connects each front portion 32,34 of the body vest 20 with each respective shoulder portion 22,24 of the body vest 20, when the buckle assemblies are engaged and adjusted.

Attached to each shoulder strap 31,33, proximate the upper edge of each front portion 32,34 of the body vest 20, is a lifting loop 36,38. The lifting loop 36,38 is formed of a strong material such as metal and has an opening therein for receiving hooks or other strong loops on the end of the rescue lines.

Attached to the bottom of each front portion 32,34 is a groin strap 26,28. The groin strap 26,28 loops around the wearer's leg and connects again to each vest front portion 32,34, respectively. Padding 25,27 is located on the groin strap 26,28 along the points where the groin strap 26,28 covers the wearer's hip and extends below the wearer's buttocks. Located at the end of the padding 25,27 on each groin strap 26,28 is a cloth compartment 90,92, which is readily opened and closed. In this particular embodiment mating Velcro pieces are used to keep the cloth compartment 90,92 closed. The cloth compartment 90,92 is used to house the unpadded portion 21,23 of each groin strap 26,28 for storage. Attached to the unpadded portion 21,23 of the groin strap 26,28 is an adjustable male portion 121,123 of a buckle assembly. Attached above the bottom of each front portion 32,34 of the body vest 20 is a female buckle 221,223 to receive the male portion 121,123 of the buckle assembly in each respective groin strap 26,28. Each groin strap 26,28 forms a loop after the buckle assemblies are engaged.

Located proximate the vertical edge of one of the front portions 34 are an upper 80 and a lower body strap 82, made from a strong flexible fabric such as nylon webbing. Attached to the opposite front body portion 32 close to its vertical edge are two male buckle portions 280,282 which correspond with the location of each respective body strap 80,82 and connect to each respective female buckle portion 180,182 to connect the two front body portions 32,34. When connected, the body straps 80,82 extend across the wearer's chest and mid-section.

Referring to FIGS. 3 and 4b, the stiffener 50 of the rescue apparatus is preferably made of a thin, lightweight, inflexible material such as metal. The stiffener 50 is preferably shaped as an elongated rectangle. The width of the stiffener 50 is slightly less than the width of the pocket 60 in the back portion 30 of the vest 20 so that it fit within the pocket 60 yet is readily removable. The length of the stiffener 50 is at least as long as the pocket 60 in the vest back portion 30. In the particular embodiment shown, the length of the stiffener 50, is from approximately the bottom of the vest back portion 30 to approximately the height of the wearer's head. It should be understood that in certain applications the stiffener 50, may be shorter. The stiffener 50 is thin, preferably about ⅛ of an inch. In order to provide adequate support, the stiffener is preferably at least 3 inches wide.

Proximate the top end, and located in the center of the stiffener 50, is a pair of small, closely spaced holes (not shown). Approximately one-third of the length down from the top of the stiffener 50 are two pairs of small, closely spaced holes (not shown) located toward each edge of the stiffener 50.

Attached to the upper portion of the stiffener 50 is a cloth envelope 52. The cloth envelope 52 is attached with stitching that passes through each pair of small, closely spaced holes (not shown) in the top portion of the stiffener 50. Sewn to one side of the fabric envelope 52 is a rear head pad 54. The rear head pad 54 is V-shaped to conform to the wearer's head. Sewn to the opposite side of the envelope 52 are two Velcro strips 56,58. The strips run vertically from the top of the cloth envelope 52 approximately two-thirds the length of the envelope. Sewn to the bottom of each Velcro strip is a vertical retainer strip 57,59. Attached to each retainer strip 57,59 are the two mating surfaces of Velcro.

Turning to FIG. 4a, the head immobilizer 40, consists of a top head pad 42 and two side head pads 44,46 having flaps 45,47. Attached to each flap 45,47 is a Velcro strip. The length of the Velcro strip corresponds to the length of the Velcro strip on the fabric envelope 52 attached to the stiffener 50 (see FIG. 4b). Attached to one side head pad 46 is a forehead strap 48, and a chin strap 49. Attached to the opposite side head pad 44 are several Velcro strips 144. Mating Velcro strips are located on both the chain strap 49 and forehead strap 48 so that each may be removably attached to the opposite side head pad 44. Located within the chin strap 49 is a chin cup 149.

It should be noted that the head immobilizer 40 can take various forms depending upon the desired use of the rescue apparatus 10. For example, the head immobilizer 40 and stiffener 50 combination could be used to provide a means to accommodate and immobilize a helmet worn by an accident victim, such as a race car driver or football player.

In operation, the body vest is slipped on to the victim with the back portion 30 placed on the victim's back and the shoulder portions 22,24 placed over the victim's shoulders. The two front body portions 32,34 are then wrapped around the sides of the victim. The front body straps 80,82, are then placed across the victim's chest and the male portions 280,282 of the buckle assembly are connected to the female buckle portions 180,182 to connect the two front body portions 32,34. The body straps 80,82 can then be adjusted by pulling the nylon webbing through the male portion 280,282 in each respective front body strap. The shoulder straps 31,33 are attached to each respective shoulder portion 22,24 by mating the male portions 131,133 of the buckle assembly 131,133, in each shoulder strap 31,33 with the female portions 122,124 of the buckle assembly in each shoulder portion 22,24. The shoulder strap 31,33 is then adjusted by pulling the strap material through the male portion 131,133, of each shoulder strap 31,33. The groin strap 26,28, is then secured. The unpadded portions 21,23, of each groin strap 26,28, are removed from the cloth compartments 90,92, in each groin strap 26,28. Each groin strap 26,28, is then threaded over the wearer's hip, below the wearer's buttocks, and through the wearer's legs and attached to the respective front body portion 32,34. Each groin strap 26,28 is attached to the front body portion 32,34 by mating the male portions 121,123 of the buckle assembly with to the female portions 221,223 of the buckle assemblies in the bottom of each front body portion 32,34. The groin strap 26,28 is adjusted by pulling the nylon webbing material through the male portions 121,123 of the buckle assembly.

If a rescuer is wearing the body vest it is very likely that the stiffener 50 and the head immobilizer 40 will not be in place. The rescuer can attach rescue lines to the lifting loops 36,38, be lifted to the accident site, remove the rescue apparatus 10 and then place the rescue apparatus 10 on the victim. This would be accomplished by going through the steps mentioned in the previous paragraph.

The stiffener 50 and the head immobilizer 40, can be attached to the vest 20 before or after placing the vest 20 on the victim. To attach the stiffener 50, it is slipped into position in the pocket 60 in the vest back portion 30. Each vertical restraining strip 57,59 is then threaded through the closest loop 72,74, in the horizontally extending restraining strap 70 and then folded back onto itself and connected to the mating piece of velcro. Each vertical restraining strip 57,59 forms a loop which prevents vertical upward movement of the stiffener 50 out of the pocket 60 of the vest 20.

In some applications, the stiffener 50, may not be desired or may be inserted after the rescue apparatus 10, is on the wearer. If the vest 20 is on the victim when the decision is made that the stiffener is needed, the thin stiffener 50 can then be inserted while the victim, for example, is lying on his back or pinned in his automobile without disrupting the victim. The width of stiffener 50 is thin, sufficient to insure adequate spinal support.

The head immobilizer 40 can then be attached to the stiffener 50 by positioning it so that the top head pad 42 is approximately at the same height as the top of the stiffener 50. Each side head pad 44,46 is then positioned along the edge of the stiffener 50. Then the Velcro attached to each flap 45,47 is attached to the Velcro strips 56,58 attached to the fabric envelope 52, on the stiffener 50. The forehead strap 48 is then wrapped around the victim's head and attached to the Velcro surface on the side head pad 44. The chin strap 49 is then attached to the Velcro surface 144 on the side head pad 44 after adjusting the chin cup 149 to fit the victim's chin. It should also be noted that the head immobilizer 40, may not be required in some rescue applications.

I claim:

1. Rescue apparatus comprising a vest of flexible material adapted to lie flat and to be wrapped about a person's torso, the vest including a back portion connected to the front body portions and straps for connecting the front body portions together around the front of the person, and the vest including shoulder portions connected to he back portions and having straps for connecting the shoulder portions to the front portions, the vest further including means defining an elongated pocket in the back portion of the vest to extend along the person's spine, the pocket being closed at its lower end and open at its upper end and an elongated, thin, flat, wide stiffener being positioned in said pocket to protect the person's spine, the stiffener extending out the upper end of the pocket to be in position to also support the person's head, said vest also including a head support for connection to the upper end of the stiffener, said support including means for connecting the support to the back upper portion of the vest.

2. The apparatus of claim 1 including means forming a pocket in said support, the pocket being closed on its upper end and open on its lower end so that the support pocket may be slipped onto the upper end of the stiffener.

3. The apparatus of claim 2 including straps attached to the head support extending downwardly for releasable connection to the vest back upper portion.

4. The apparatus of claim 3 including a horizontally extending retainer strap secured to the vest back upper portion and forming a loop through which the straps on the head support can extend, said head support straps including fasteners means whereby the head support straps may extend through the vest loop and be looped back upwardly on itself and fasten to itself to thereby form a connection to the vest.

5. The apparatus of claim 1 including a head protector to be positioned on a person's head, said protector including means for releasably attaching the protector to the head support.

6. The apparatus of claim 5 wherein said head protector includes cushioned elements that may be wrapped around a person's head when the head is resting on the head support.

7. The apparatus of claim 1 including groin straps for forming loops around a person's legs in the groin area having means for connection to the front and back portions of the vest so that the person may be lifted by means of the vest.

8. The apparatus of claim 1 or 7 including lifting loops attached to the front portion of the vest.

9. Rescue apparatus comprising a vest comprising a back portion and two front and side portions connected to the back portion, and shoulder strap portions connected to the back portion, said vest portions comprising a flexible fabric envelope of nylon or other such material and inner cushion material, the vest further including releasable straps for connecting the front portions of the vest after a person has been placed on the vest while the vest is lying flat, and straps for joining the shoulder portions to the front portions, said back portion including an elongated pocket extending from the lower edge of the vest back portion to the upper edge of the vest back portion, the pocket being at least three inches wide; a thin, flat, elongated stiffener positioned in said pocket and extending out the upper end of the pocket, the stiffener providing support for a person's spine and head; a head support, removably positioned on the end of the stiffener, extending out of the vest pocket pocket, including straps on the head support releasably connecting the head support to the vest so that the head support is secured to the stiffener; and a head protector releasable attached to the head support.

10. A method for applying a rescue apparatus, said rescue apparatus comprising a vest of flexible material including a back portion connected to the front body portions and straps for connecting the front body portions together around the front of the person, and the vest further including shoulder portions connected to the back portion and having straps for connecting the shoulder portions to the front portions, the vest further including means defining an elongated pocket in the back portion of the vest to extend along the person's spine, the pocket being closed at its lower end and open at its upper end to receive an elongated, thin, wide stiffener to protect the person's spine, said method comprising:

placing said vest on the victim;

attaching the straps for connecting the front body portions together and for connecting the shoulder portions to the front body portion;

inserting the stiffener into the elongated pocket in the back portion of the vest;

said vest further includes a head support for connection to the upper end of the stiffener, said support including means connecting the support to the back upper portion of the vest, and said method further comprising the steps of:

positioning the stiffener so that the head support is behind the victim's head; and connecting the head support to the back upper portion of the vest.

11. The method of claim 10 including the steps of connecting a pair of straps to form loops around the person's legs with the straps connected to the front and back portions of the vest so that a person may be lifted by way of the groin strap and lifting loops attached to the front portion of the vest.

* * * * *